United States Patent
Tsuji et al.

(10) Patent No.: US 10,010,298 B2
(45) Date of Patent: Jul. 3, 2018

(54) PERIODONTAL DISEASE TESTING APPARATUS AND IMAGE PROCESSING PROGRAM USED THEREIN

(71) Applicant: MEDIA CO., LTD., Tokyo (JP)

(72) Inventors: Hironobu Tsuji, Tokyo (JP); Yosuke Tsuji, Tokyo (JP); Tatsuro Hayashi, Tokyo (JP)

(73) Assignee: Media Co., Ltd., Tokyo (JP)

( * ) Notice: Subject to any disclaimer, the term of this patent is extended or adjusted under 35 U.S.C. 154(b) by 0 days.

(21) Appl. No.: 14/976,075

(22) Filed: Dec. 21, 2015

(65) Prior Publication Data
US 2016/0100811 A1  Apr. 14, 2016

Related U.S. Application Data

(63) Continuation-in-part of application No. PCT/JP2013/067924, filed on Jun. 28, 2013.

(51) Int. Cl.
*G06K 9/00* (2006.01)
*A61B 6/14* (2006.01)
(Continued)

(52) U.S. Cl.
CPC .......... *A61B 6/14* (2013.01); *A61B 6/032* (2013.01); *A61B 6/466* (2013.01); *A61B 6/5205* (2013.01); *A61B 6/5223* (2013.01); *A61B 6/5235* (2013.01)

(58) Field of Classification Search
None
See application file for complete search history.

(56) References Cited

U.S. PATENT DOCUMENTS

| | | | |
|---|---|---|---|
| 2005/0018886 A1* | 1/2005 | Kim | A61B 6/14 382/128 |
| 2009/0052617 A1* | 2/2009 | Sadakane | A61B 6/032 378/38 |
| 2014/0126686 A1* | 5/2014 | Sadakane | A61B 6/145 378/13 |

FOREIGN PATENT DOCUMENTS

| | | |
|---|---|---|
| EP | 2452652 A1 | 5/2012 |
| JP | 7-334702 A | 12/1995 |

(Continued)

OTHER PUBLICATIONS

Diagnostic Strategies of Periodontal Diseases, ISBN978-4-263-45427-5.

(Continued)

*Primary Examiner* — Nancy Bitar
(74) *Attorney, Agent, or Firm* — Manatt, Phelps & Phillips, LLP

(57) ABSTRACT

A periodontal disease testing apparatus of the present invention includes: an X-ray CT scanner photographing a portion including a tooth, a gingiva, and alveolar bone within an oral cavity to generate volume data of the portion; region setting means setting a related region of a subject tooth based on the volume data; defining means defining a principal axis of the subject tooth; correcting means correcting the related region so as to align the principal axis of the subject tooth with a normal direction of a cross-section of an X-ray CT image; multi-planar reconstruction image generating means generating a multi-planar reconstruction image of the corrected related region; means for generating developed image and the like transforming a coordinate of the related region to generate a developed image and a rotated image; and navigating means indicating correspondences of a spatial coordinate among the multi-planar reconstruction image, the developed image, and the rotated image.

6 Claims, 21 Drawing Sheets

(51) Int. Cl.
A61B 6/00 (2006.01)
A61B 6/03 (2006.01)

(56) References Cited

FOREIGN PATENT DOCUMENTS

| | | |
|---|---|---|
| JP | 11-353306 A | 12/1999 |
| JP | 2005-538766 A | 12/2005 |
| JP | 2006-181109 A | 7/2006 |
| JP | 2007-130240 A | 5/2007 |
| JP | 2008-107981 A | 5/2008 |
| JP | 2008-229322 A | 10/2008 |
| JP | 2008-304422 A | 12/2008 |
| JP | 2009-247535 A | 10/2009 |
| JP | 2010-504169 A | 2/2010 |
| JP | 2010-148590 A | 7/2010 |
| JP | 2010-246855 A | 11/2010 |
| WO | 03/037189 A2 | 5/2003 |
| WO | 2004/025566 A1 | 3/2004 |
| WO | 2008/036766 A1 | 3/2008 |

OTHER PUBLICATIONS

Diagnostic Image Examination Method: Practical Implementation of X-ray CT, the Latest Edition, ISBN4-86003-358-2.
Matsuura Tomoji, Measuring Crown Form According to Crown and Root Axes of the Maxillary Anterior Teeth, and Its Prosthodontic Significance, Kyushu-Shika-Gakkai-zasshi, 35 (3), 396-415, 1981.

* cited by examiner

PERIODONTAL DISEASE TESTING APPARATUS AND IMAGE PROCESSING PROGRAM USED THEREIN

RELATED APPLICATIONS

This application is a continuation-in-part application of, and claims priority to, PCT application number PCT/JP2013/067924 filed Jun. 28, 2013 (International Publication number WO2014/207932), which is hereby incorporated by reference.

TECHNICAL FIELD

The present invention is in the field of diagnosis and treatment of periodontal disease. More specifically, the present invention relates to a method and apparatus for determining the stage of periodontal disease based on three dimensional information of teeth obtained from an X-ray CT image and treating periodontal disease.

BACKGROUND ART

Periodontal disease is a disease that affects a portion around a tooth, that is, the gums (gingiva), the alveolar bone, the periodontal ligament, and the cementum portion below the gums. However, in general, periodontal disease indicates inflammatory disease affecting a portion around a tooth, which makes up 90% or more of the patients. Accordingly, a common periodontal disease is caused by bacteria such as *Porphyromonas gingivalis*. The present invention also focuses on a common periodontal disease. Hereinafter, a common periodontal disease will be referred to as "periodontal disease", while other periodontal diseases will be referred to as "special periodontal disease".

Hereinafter, the stages of periodontal disease will be described. Although a mandibular tooth, whose root apex points downward is taken as an example, the same applies to a maxillary tooth. FIG. 1 is a cross-sectional view schematically showing a sound tooth, and FIG. 2 is a cross-sectional view schematically showing a tooth with periodontal disease. As shown in FIG. 1, a sound tooth 30 has its root 31 supported by a periodontal ligament 32*a*, an alveolar bone 35, and gums (gingiva) 32. A space between the root 31 and the gums 32 is called a periodontal pocket 45 (hereinafter, simply referred to as "pocket" or "gingival sulcus").

If affected by periodontal disease, the gums (or gingiva) 32 becomes red and swollen, the periodontal ligament 32*a* is breached, and as shown in FIG. 2, blood and pus 48 ooze from the periodontal pocket 45 to start melting the alveolar bone 35. A depth of the pocket 45 from the gums top 46 to a pocket bottom 47 is about 0 to 1 mm in the case of a sound tooth, while the depth is deepened with the progress of periodontal disease in the case of a tooth 30 affected by periodontal disease.

Before starting the treatment of periodontal disease, the tooth is tested to determine to what extent the current symptom has progressed first, and then, how the symptom will develop needs to be determined. Various testing methods have been developed so far. The currently used major testing methods include those by probing, X-ray, and bacteria.

In the probing test method, a probe (a needle for test) is inserted into the pocket 45, and the state of the symptom is found out while measuring the depth of the pocket 45. This is the simplest method of the above, and can be applied to the symptoms at any stage. The method includes one-point method of measuring at the deepest portion, four-point method of measuring at mesial and distal sides and buccal and lingual sides, and six-point method of measuring at two more points in addition to the foregoing four points.

In the testing method using X-ray, the bone level (indicating the level of the crest of the alveolar bone supporting the tooth between the root apex and the cement-enamel boundary) and the outline of the alveolar bone 35 are grasped from a radiograph (a dental radiograph or a panoramic radiograph) of the tooth 30 and the periodontal tissue.

In the testing method using a bacteriological examination, pathogenic bacteria of periodontal inflammation is examined to determine activity and progressiveness of periodontosis. That is, it is considered that different bacteria have different degrees of pathogenicity, and therefore the activity can be determined by identifying the bacteria.

Physiological mobility of a sound tooth, which is usually within a range of 0.2 mm, is a total deformation of the periodontal soft tissue (e.g., gingiva and the periodontal ligament) and the alveolar bone. The degree of mobility, which increases with the progress of periodontal disease, is increased either by an inflammatory change in the periodontal tissue (refer to FIG. 3) or by reduction in bone level (refer to FIG. 4). In the former case, the mobility can be improved by removing the cause of the inflammation, while in the latter case, the mobility is hardly lessened unless the periodontal tissue is renewed. In general, a plurality of factors comprehensively cause a tooth to move. Accordingly, it is important to discriminate between the mobility that can be lessened by periodontal tissue treatment (the mobility caused by inflammation) and the mobility that cannot be lessened (the mobility caused by quantitative decrease of the supporting tissue) (refer to Non Patent Literature 1).

By the way, the degree of the bone level reduction considerably varies among the mesial and distal sides and buccal and lingual sides of the same tooth. Observation of the convex and concave shapes of the bone level is a significant observation that helps selecting a remedy or predicting whether the periodontal ligament can be renewed. Bone level reductions progressing uniformly within the oral cavity are called horizontal bone defects, and those progressing quickly at a particular portion are called vertical bone defects. Vertical bone defects are further separated into three-wall, two-wall, and one-wall vertical bone defects by the number of side bone walls surrounding an exposed root surface at bone defect portion.

In treatment of a root surface, which is exposed where the bone has a vertical defect, dentists sometimes cannot control instruments sufficiently due to surrounding bone walls. In the case of vertical bone defects, the periodontal ligament remains not only at a portion at and close to the root apex of the tooth having the defect but also at the sides in a manner close to each other. Accordingly, it is considered that the periodontal ligament is easily renewed at the root surface exposed inside the defect. In particular, renewal of the periodontal ligament can be expected with a high probability at the portion of three-wall bone defect. The renewal can be expected also in the case of two-wall bone defect, if the width of the defect is narrow. However, renewal is considered to be difficult in the case of one-wall bone defect, in which the pocket is likely to remain, and thus the remaining bone wall is often removed by an osteoplasty.

Thus, it is important to correctly grasp the convex-concave shape of the alveolar bone for it affects the treatment of periodontal disease. Though the bone level can be grasped from a radiograph as described above, it is difficult to completely understand the three-dimensional convex-concave shape of the bone level because in a radiograph a tooth and the periodontal tissue is drawn by being projected onto a two-dimensional plane. Accordingly, an approach is adopted clinically in which the three-dimensional state of the bone level is inferred from, for example, values obtained by probing test. However, it is pointed out that probing measurement values themselves have a reproducibility problem. That is to say, it has been hard for dentists to correctly grasp the convex-concave shape of the bone level.

In recent years, more and more dental clinics have adopted computer tomographic equipment (dental X-ray CT scanner) tailored for dental use. Using a dental X-ray CT scanner, a precise three-dimensional image of a tooth and a jawbone can be obtained. Thus, a dental X-ray CT scanner is now essential for safely performing sophisticated dentistry such as implant dentistry.

A three-dimensional image obtained from a three-dimensional space of the living body contains not only image data of a surface of a three-dimensional object but also image data of a point inside the object, so the three-dimensional image is particularly called "volume data". Medical diagnostic imaging apparatus for generating volume data is not limited to a dental X-ray CT scanner and includes various devices such as a medical X-ray CT scanner, a three-dimensional ultrasonic apparatus, a nuclear magnetic resonance apparatus, and a positron emission tomography apparatus.

Although volume data is image data of a point inside a three-dimensional space, an image display apparatus (monitor) for observing the data has a two-dimensional display surface. As a result, in order to appropriately draw the structure of a three-dimensional object to be observed onto the monitor, the volume data needs to be processed with image processing techniques into a two-dimensional image. Examples of a process of converting volume data into a two-dimensional image typically include multi-planar reconstruction, maximum intensity projection, shaded surface display, and volume rendering, which are known techniques (refer to Non Patent Literature 2).

Basic multi-planar reconstruction used for diagnostic imaging involves three image cross-sections: an axial cross-section obtained by horizontally cutting the body axis (or principal axis) which is set in a vertical direction; a coronal cross-section obtained by cutting an object widthwise in the left/right direction with respect to the body axis; and a sagittal cross-section obtained by cutting an object lengthwise in the front/rear direction with respect to the body axis. Hereinafter, the axial cross-section, the coronal cross-section, and the sagittal cross-section will be respectively referred to as an "A cross-section", a "C cross-section", and an "S cross-section" for the sake of simplicity.

It is, needless to say, important to manipulate the volume data for doctors to easily make a diagnosis, and a technique is disclosed in which displaying method has been improved to the shape of an object to be observed. For example, a technique has been described in which a medical image of a tube-like part such as the esophagus is converted geometrically and output to display means as a developed view for easily making a diagnosis on the state of the inner surface (refer to Patent Literature 1). Any point of the A, C, and S cross-sections can be displayed from volume data by a known technique, and navigation technique has also been described which helps understanding the correspondences among the cross-sections (refer to Patent Literature 2). According to Paten Literature 2, using both a diagnosis object image and a standard template, when a user specifies any spatial coordinate, A, C, and S cross-sections corresponding to the position of the coordinate are displayed, and also the correspondences among the cross-sections are shown as an intersection of a cross line.

Volume data obtained by photographing the inside of the oral cavity with a dental X-ray CT scanner contains detailed morphology information on a tooth and the surrounding tissue (e.g., the alveolar bone). The convex-concave shape of the alveolar bone, if understood from the volume data, can be used for setting up a treatment program for periodontal disease. In the dental and dental surgery fields, a technique for determining implantation site of implants or performing an orthodontic treatment has been described in which, if an anatomical feature point (landmark) is placed according to an arch shape of the row of teeth, the position of a cut section is determined based on the landmark, thereby showing the cut section (refer to Patent Literature 3). There have been no techniques disclosed, however, of manipulating volume data for easily making a diagnosis on the convex-concave shape of the alveolar bone.

CITATION LIST

Patent Literature

Patent Literature 1: Japanese Patent Laid-Open No. 2006-181109
Patent Literature 2: Japanese Patent Laid-Open No. 2009-247535
Patent Literature 3: Japanese Patent Laid-Open No. 2010-148590
Patent Literature 4: Japanese Patent Laid-Open No. 11-353306
Patent Literature 5: Japanese Patent Laid-Open No. 2008-304422
Patent Literature 6: National Publication of International Patent Application No. 2005-538766
Patent Literature 7: National Publication of International Patent Application No. 2010-504169
Patent Literature 8: Japanese Patent Laid-Open No. 2010-246855
Patent Literature 9: Japanese Patent Laid-Open No. 2008-107981

Non Patent Literature

Non Patent Literature 1: Diagnostic Strategies of Periodontal Diseases, ISBN978-4-263-45427-5
Non Patent Literature 2: Diagnostic Image Examination Method: Practical Implementation of X-ray CT, the Latest Edition, ISBN4-86003-358-2
Non Patent Literature 3: Matsuura Tomoji, Measuring Crown Form According to Crown and Root Axes of the Maxillary Anterior Teeth, and Its Prosthodontic Significance, Kyushu-Shika-Gakkai-zasshi, 35 (3), 396-415, 1981, all of which are hereby incorporated by reference.

SUMMARY OF INVENTION

Technical Problem

The present invention has been made to solve the foregoing problems. That is, an object of the present invention is to provide a volume data manipulating technique with which a user can freely display a convex-concave shape of an alveolar bone onto a display surface of a display device for easy diagnosis of periodontal disease.

Solution to Problem

A first aspect of the present invention includes: an X-ray CT scanner photographing a portion including a tooth, a gingiva, and alveolar bone within an oral cavity to generate volume data of the portion; region setting means setting a related region of a subject tooth based on the volume data; defining means defining a principal axis of the subject tooth; correcting means correcting the related region so as to align the principal axis of the subject tooth with a normal direction of a cross-section of an X-ray CT image; multi-planar reconstruction image generating means generating a multi-planar reconstruction image of the corrected related region; a means for generating developed image and the like transforming a coordinate of the related region to generate a developed image and a rotated image; and navigating means indicating correspondences of a spatial coordinate among the multi-planar reconstruction image, the developed image, and the rotated image.

In a second aspect of the present invention, the first aspect of the present invention may be configured so that when a user inputs two feature points with respect to the subject tooth, the region setting means sets a cubic region with the input point at the center.

In a third aspect of the present invention, the first aspect of the present invention may be configured so that the defining means defines the principal axis with a segment connecting two feature points input by the user as a unit vector of the principal axis.

In a fourth aspect of the present invention, the first aspect of the present invention may be configured so that the correcting means performs a rotation correction process on the related region so as to align the principal axis with a normal vector of cross-sections constituting an A tomogram image of the X-ray CT image.

In a fifth aspect of the present invention, the first aspect of the present invention may be configured so that the multi-planar reconstruction image generating means generates a tomogram image with which an A cross-section, a C cross-section, and an S cross-section corresponding to any position of the related region after an application of the rotation correction process can be displayed.

In a sixth aspect of the present invention, the first aspect of the present invention may be configured so that the means for generating developed image and the like creates cross-sections while rotating the related region after the application of the rotation correction process about the principal axis and overlays the cross-sections such that the cross-sections have the same distance from the principal axis, thereby generating a tomogram image.

In a seventh aspect of the present invention, the first aspect of the present invention may be configured so that when a part or all of five screens of an A cross-section, a C cross-section, an S cross-section, a cross-section of the developed image, and a cross-section of the rotated image are displayed, if a user specifies a position on any one of the screens, the navigating means switches remaining screens to cross-sections which show the position specified by the user and show the positions with intersections of cross lines or a contacting part of a circle and a half line.

An eighth aspect of the present invention is an image processing program performed in the first aspect of the present invention and includes a module for setting a related region of a subject tooth based on the volume data; a module for defining a principal axis of the subject tooth; a module for correcting the related region so as to align the principal axis of the subject tooth with a normal direction of a cross-section of the X-ray CT image; a module for generating a multi-planar reconstruction image of the corrected related region; a module for transforming a coordinate of the related region to generate a developed image and a rotated image; a module for indicating correspondences of a spatial coordinate among the multi-planar reconstruction image, the developed image, and the rotated image.

Advantageous Effects of Invention

According to the present invention, the convex-concave shape of the alveolar bone along the entire circumference of a subject tooth can be observed in a manner which allows a doctor to diagnose easily. The process does not include an inference by a dentist like those in a conventional radiograph or a probing test. This allows grasping the bone level more objectively and quantitatively, contributing to improvement of diagnosis and a technique of treating periodontal disease.

DESCRIPTION OF EMBODIMENTS

Hereinafter, an embodiment of the present invention will be described based on the attached drawings.

Figure 1:
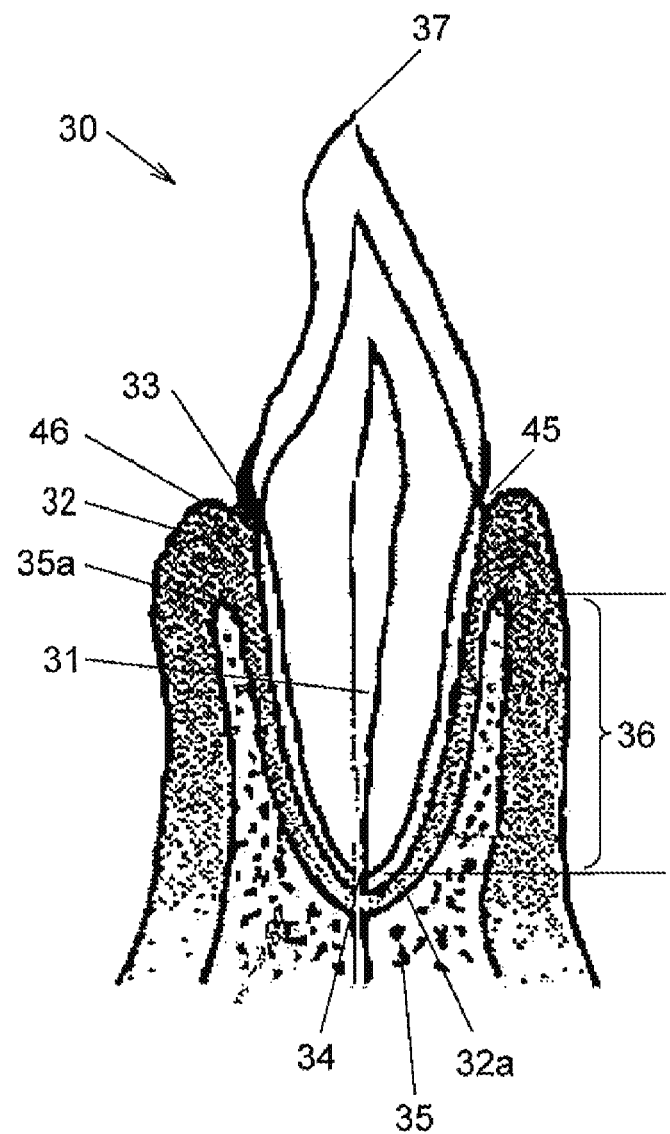
FIG. 1 is a cross-sectional view schematically showing a sound tooth.
Figure 2:
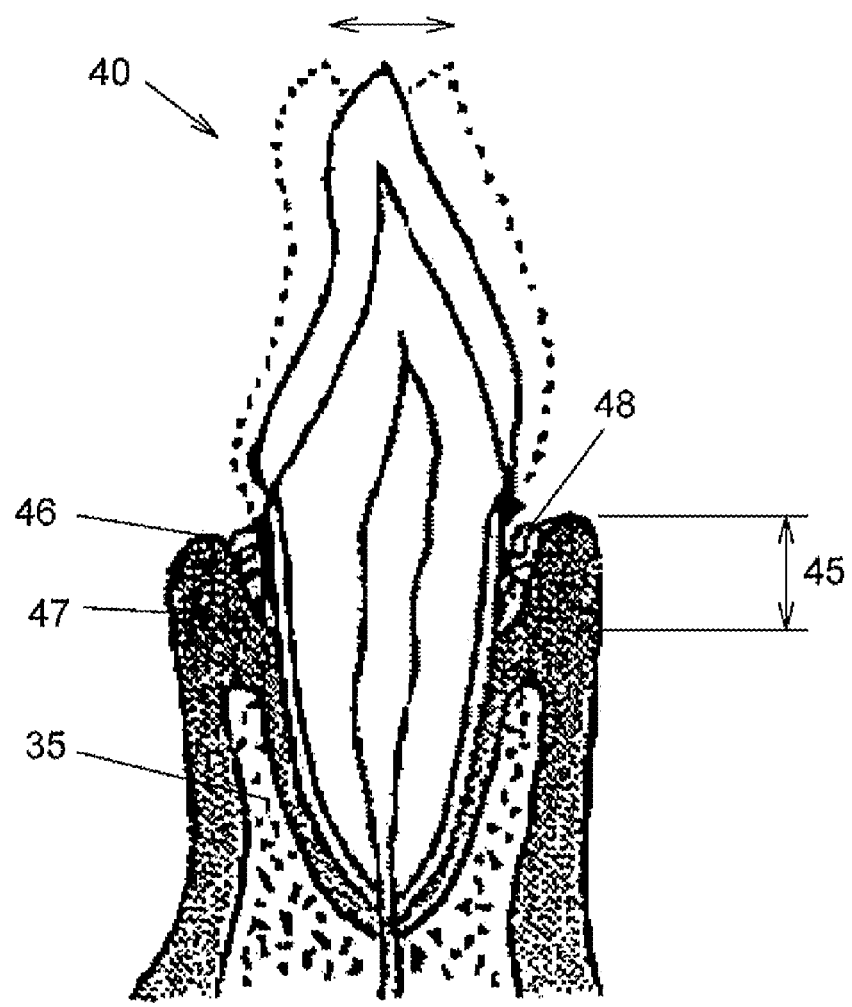
FIG. 2 is a cross-sectional view schematically showing a tooth affected by periodontal disease.
Figure 3:
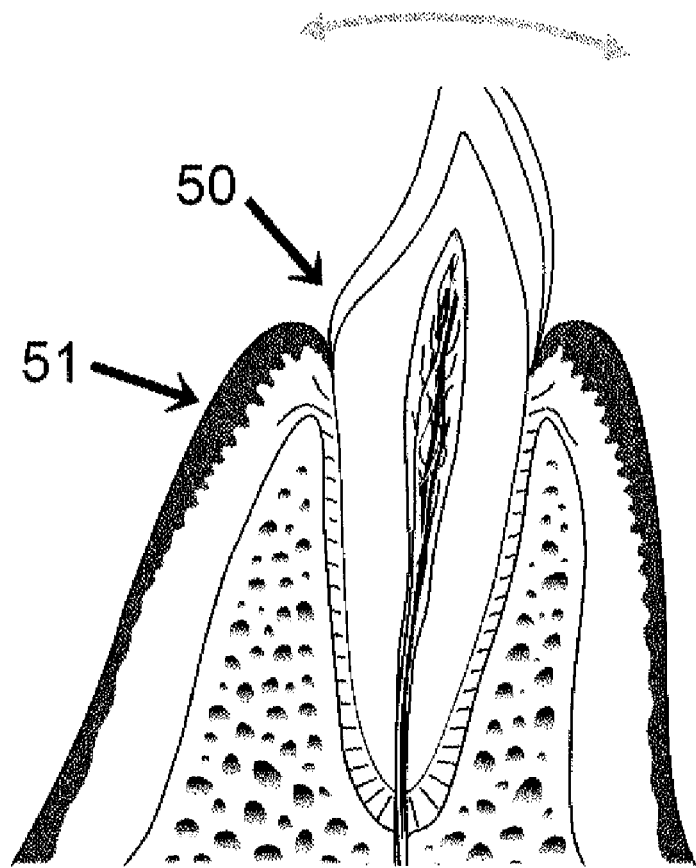
FIG. 3 is a view explaining periodontal disease caused by an inflammatory change in periodontal tissue.
Figure 4:
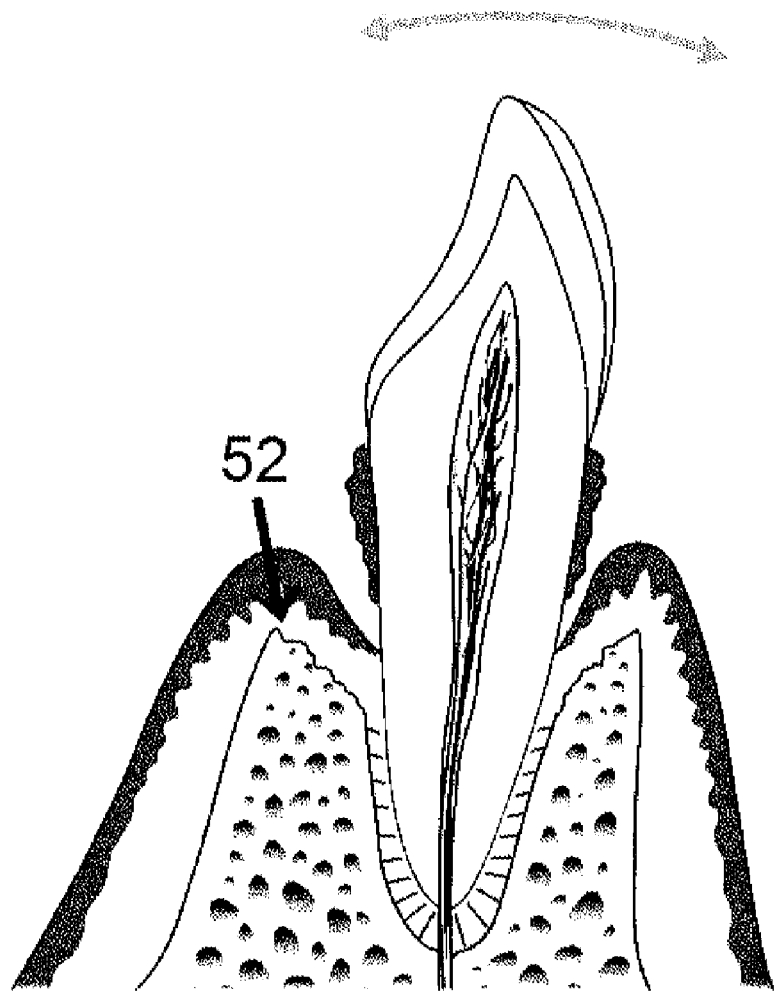
FIG. 4 is a view explaining periodontal disease caused by a reduced bone level.
Figure 5:
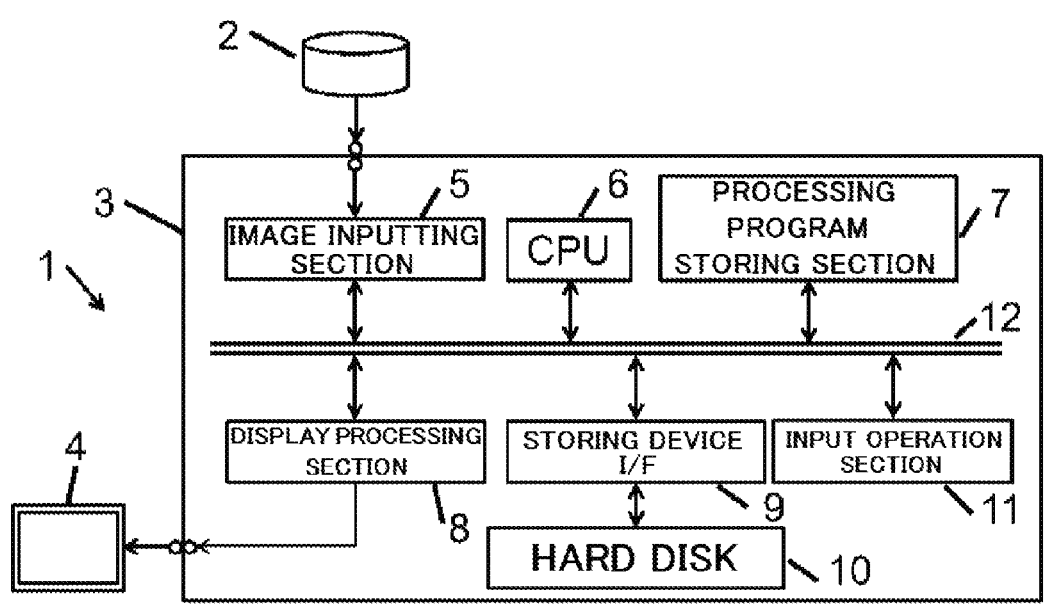
FIG. 5 is a view schematically explaining a system used in the present invention to which a DICOM file, a computer, and a monitor are connected.

A medical image processing apparatus 1 shown in FIG. 5 is constituted by a DICOM file 2, an alveolar bone convex-concave shape visualization device 3, an embodiment of the present invention, constituted by, for example, a personal computer performing image processing on the DICOM file 2, and a display monitor 4 displaying an image processed by the alveolar bone convex-concave shape visualization device 3.

The DICOM file 2 is obtained by photographing an oral three-dimensional space of a living body with a dental X-ray CT scanner. The term DICOM means a standard that defines a format of a medical image and a communication protocol between medical imaging apparatuses handling such images, and contains photographing environment information (e.g., a name of the photographing device, a name of the patient, a patient ID, and photographing conditions) and volume data. The DICOM file 2 is input into the alveolar bone convex-concave shape visualization device 3.

The alveolar bone convex-concave shape visualization device 3 includes an image inputting section 5 for reading a DICOM file to extract volume data and meta-information such as a photographing environment, a CPU 6 as a central processing unit for image-processing the volume data extracted by the image inputting section 5, and a processing program storing section 7 for storing a processing program (control program) for the CPU 6 to perform the image-processing.

In addition, the alveolar bone convex-concave shape visualization device 3 includes a hard disk 10 as a storing device for storing via a storing device interface 9, for example, the volume data and the meta-information extracted by the image inputting section 5 and the volume data and the meta-information processed by the CPU 6, a display processing section 8 carrying out a displaying process for displaying, for example, the volume data processed by the CPU 6, and an input operation section 11 including, for example, a mouse with which a user inputs data such as image processing parameters or performs instruction operation.

Then, a picture signal generated by the display processing section 8 is displayed on the display monitor 4, and a processed image appears on a display screen of the display monitor 4. Here, the image inputting section 5, the CPU 6, the processing program storing section 7, the display processing section 8, the storing device interface 9, and the input operation section 11 are connected to each other through a data path 12.

Figure 6:
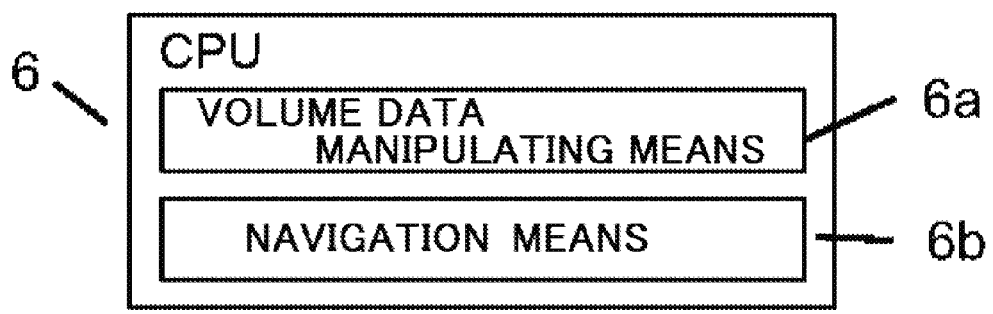
FIG. 6 is a view explaining an image processing function by a CPU.

As shown in FIG. 6, the CPU 6 of the alveolar bone convex-concave shape visualization device 3 includes developed image outputting means (function) 6a for outputting a developed image of a subject tooth to the display monitor 4 and navigation means (function) 6b for showing on the screen positional relations of a spatial coordinate among a developed image, a multi-planar reconstruction image, and an image obtained by imaging the developed image while rotating the developed image around the principal axis of the subject tooth (hereinafter, referred to as rotated image). The display surface of the display monitor 4 shows each cross-section of a developed image, a rotated image, and a multi-planar reconstruction image, and a user is navigated on each display screen by information on the positional relation of the spatial coordinate of each screen.

Figure 7A:
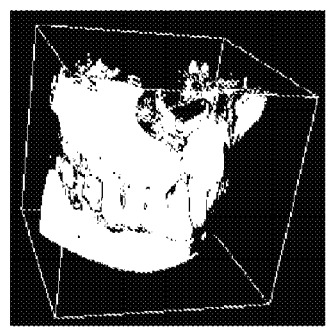
FIGS. 7a to 7e are views each showing an example of imaging volume data obtained from an oral three-dimensional space of a living body using a typical process.
Figure 7B:
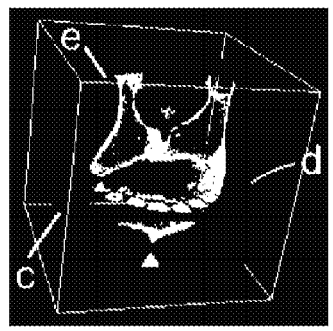
Figure 7C:
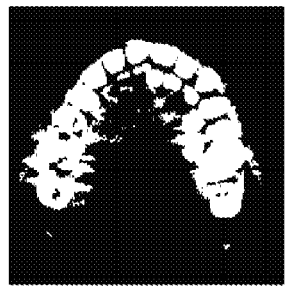
Figure 7D:
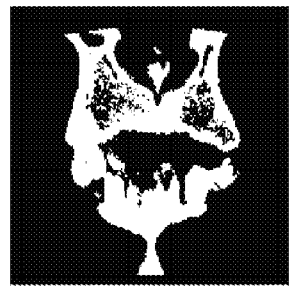
Figure 7E:
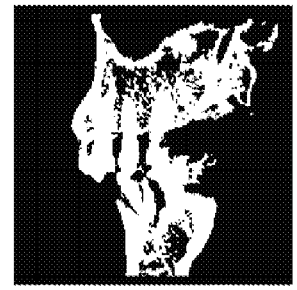

FIGS. 7a to 7e shows an example of imaging the volume data obtained from the oral three-dimensional space of a living body and input into the alveolar bone convex-concave shape visualization device 3 using a typical process. FIG. 7a shows a surface of the object which is obtained by generating an isosurface based on the density information of the volume data. FIG. 7b shows a set of cross-sections in three-directions (FIG. 7c: A cross-section, FIG. 7d: C cross-section, and FIG. 7e: S cross-section) of the same volume data in the same coordinate system as that of FIG. 7a.

Although the volume data contains detailed three-dimensional morphology information as described above, the monitor, which shows an image two-dimensionally, cannot show the information at a time. In general, shaded surface display (FIG. 7a) or volume rendering is used for grasping a general outline of volume data, and multi-planar reconstruction (FIGS. 7b to 7d) is used when requiring precise information such as for positioning in surgery.

In the embodiment, first the image inputting section 5 extracts the volume data from the oral three-dimensional space of a living body, receives input operations of the user about a subject tooth and its principal axis. Next, the volume data is manipulated by geometrical coordinate transformation and processed to generate a tomogram image (a rotated image) obtained by rotating the object around the principal axis or a tomogram image (a developed image) obtained by developing the object along the entire circumference at the same distance from the principal axis. Then, these tomogram images are shown on the display monitor 4. However, although the convex-concave shape of the alveolar bone can be understood from these tomogram images, these tomogram images are unfamiliar to doctors, and thus the doctors can hardly understand the correspondences between these images and the volume data. Therefore, the object is shown in multi-planar reconstruction images (an axial cross-section, a coronal cross-section, and a sagittal cross-section) to show also on the multi-planar reconstruction images a position spatially the same as that of any coordinate on the rotated image or the developed image. By comprehensively referencing the rotated image, the developed image, and the multi-planar reconstruction images, doctors can grasp both the convex-concave shape of the alveolar bone and which point within the volume data they are observing. These means are achieved by software, and therefore the CPU 6 reads the processing program stored in the processing program storing section 7 and performs the processing procedures shown in FIG. 8 in accordance with the processing program.

Figure 8:
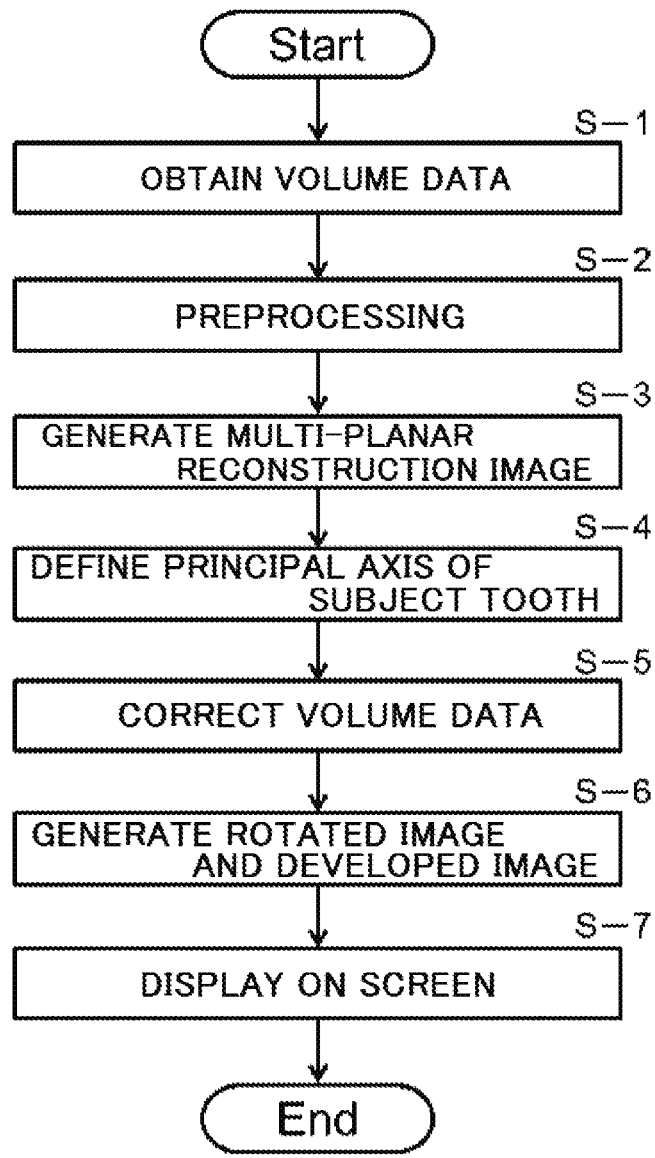
FIG. 8 is a view showing a process flow of the present invention.

Referring to FIG. 8, operation of the embodiment will be described. When the alveolar bone convex-concave shape visualization device 3 starts the operation, the CPU 6 reads the processing program from the processing program storing section 7 and starts the processes in accordance with the processing program. In step S1, the CPU 6 obtains the volume data of the oral three-dimensional space of a living body from the DICOM file 2 via the image inputting section 5.

In the next step S2, the obtained volume data undergoes preprocessing. The volume data just obtained from the DICOM file does not always have equal spatial resolutions three-dimensionally in all directions as it is. Therefore, the volume data undergoes interpolation so that the resulting volume data has equal spatial resolutions in all directions. The interpolation is performed by the method described in Patent Literature 4, for example. At this time, noise reduction processing, sharpening processing, and gray value correction processing may be performed for improving the image quality of the volume data. Known techniques are used in step S2, and explanations of interpolation or preprocessing will be omitted.

Figures 9A, 9B, 9C:
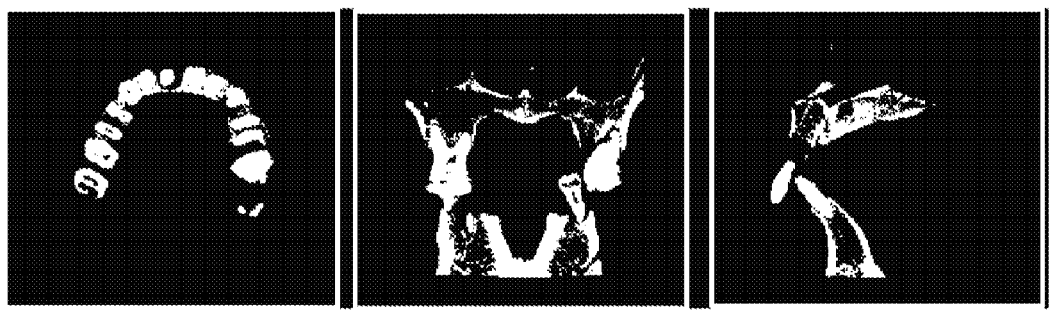
FIGS. 9a to 9c are views showing an example of displaying A, C, and S cross-sections which correspond to the position of an arbitrary spatial coordinate of a multi-planar reconstruction image generated from the volume data.

In step S3, a multi-planar reconstruction image is generated from the volume data, and A, C, and S cross-sections each corresponding to the position of any spatial coordinate are displayed. Display examples of A, C, and S cross-sections are shown in FIGS. 9a to 9c. FIGS. 9a to 9c shows A, C, and S cross-sections at the central position of the volume data. Generating a multi-planar reconstruction image from volume data and displaying A, C, and S cross-sections of any position based on the volume data is a known technique, and description thereof will be omitted. When the user presses, for example, "←" key or "→" key of a keyboard on the cross-sections, the position of the cross-section to be displayed can be moved, thereby displaying a cross-section of any position according to the user's input.

Figure 10:
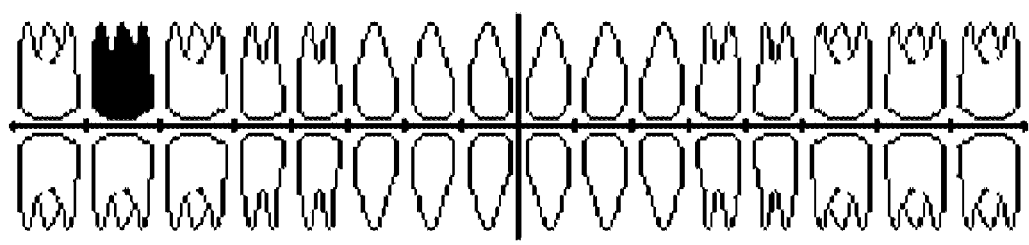
FIG. 10 is a view showing an example of a screen for specifying a subject tooth.

In step S4, the principal axis of a subject tooth is defined. The subject tooth is defined first. For example, a tooth number illustration screen as in FIG. 10 is displayed on the display monitor 4, and the user clicks the left mouse button on an illustration of a tooth to be processed. Then, the CPU 6 regards the tooth as the subject tooth. The illustration of the tooth specified as the subject tooth becomes colored on the screen.

Next, the principal axis of the subject tooth is defined. There are several theories academically about definition of a tooth axis, including an axis based on the crown, an axis based on the root, and an axis comprehensively based on both the crown and the root (refer to Non Patent Literature 3). Also, there is disclosed a method for defining a tooth axis utilizing image-processing (refer to Patent Literatures 6 and 7). Further, there is also disclosed a technique for displaying a cross-section including the tooth axis (refer to Patent Literature 8). It is to be noted that the apparatus of Patent Literature 8 is not equipped with a function of defining a tooth axis, and the definition of a tooth axis is left to a user. Thus, there are various views and approaches about the definition of a tooth axis, and there is no consensus on it.

Figure 11:
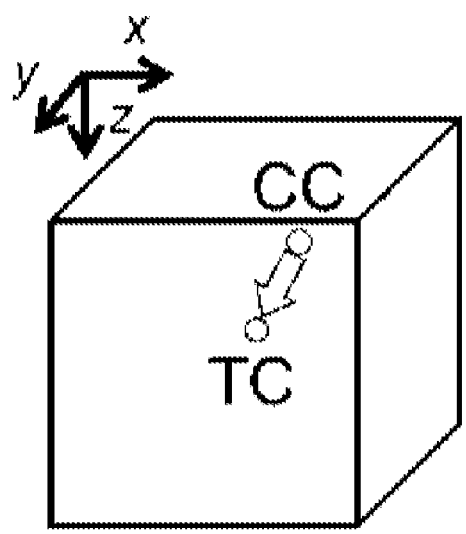
FIG. 11 is a view explaining definition of a principal axis of the subject tooth.

In view of the fact that probing test of periodontal disease is carried out with only the crown visible to the dentist, in the embodiment, the axis based on the crown is adopted and the axis is called the principal axis of the subject tooth. A view for explaining the definition of the principal axis of the subject tooth is shown in FIG. 11. First, the user inputs two coordinates of "Crown Centroid: $CC = (cc_x, cc_y, cc_z)$" and "Tooth Centroid: $TC = (tc_x, tc_y, tc_z)$". The user inputs the two points while moving the display positions of the cross-sections (the A, C, and S cross-sections) of the multi-planar reconstruction images generated in step S3. On receiving the input of the two points, the CPU 6 defines a vector "m" of the principal axis of the subject tooth by the following expression (1).

$$\vec{m} = \frac{(tc_x - cc_x, tc_y - cc_y, tc_z - cc_z)}{\sqrt{(tc_x - cc_x)^2 + (tc_y - cc_y)^2 + (tc_z - cc_z)^2}} \quad \text{[Expression 1]}$$

Next, a related region of the subject tooth is specified. The related region is defined as a region shaped in a cube with a side of length n mm (n is a positive integer) with its center at the coordinate of the TC. A track bar is displayed on the display monitor 4. The user regulates the n value while operating the track bar to specify the related region such that the related region includes the subject tooth and the contact part of the subject tooth and teeth adjacent to the subject tooth. In the following steps, the process is performed only in the related region of the subject tooth, thereby reducing computation costs of the CPU 6.

Figure 12:
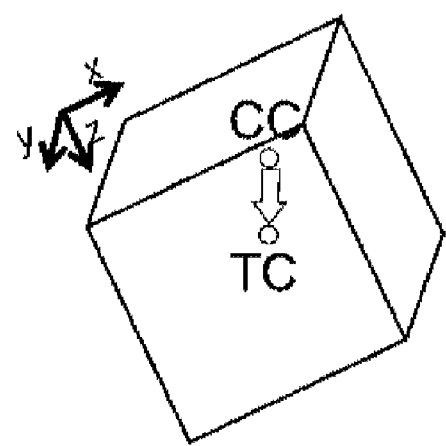
FIG. 12 is a view explaining correction of the principal axis of the subject tooth.

In step S5, the volume data is corrected. Specifically, the related region of the subject tooth is rotated to correct so as to align the principal axis of the subject tooth with the body axis of the X-ray CT image (the z axis orientation in FIG. 11 or the reverse orientation of z axis) (refer to FIG. 12). It is to be noted that the principal axis of the subject tooth may be corrected into two orientations because the relative positions of the crown and the root of a maxillary tooth is reversed in a mandibular tooth, and thus the orientation of the principal axis is different from each other. Taking the vector of the body axis of the X-ray CT image as n, the vector n is defined by the following expression (2).

$$\vec{n} = \begin{cases} (0.0, 0.0, -1.0) & \text{when the subject tooth is a maxillary tooth} \\ (0.0, 0.0, 1.0) & \text{when the subject tooth is a mandibular tooth} \end{cases} \quad \text{[Expression 2]}$$

The vector v of the rotation direction and the rotation angle θ, which are used as parameters for correcting the principal axis of the subject tooth, are respectively calculated in accordance with the following expressions (3) and (4).

$$\vec{v} = \frac{\vec{m} \times \vec{n}}{|\vec{m} \times \vec{n}|} \quad \text{[Expression 3]}$$

$$\theta = \cos^{-1}\left(\frac{\vec{m} \cdot \vec{n}}{|\vec{m}||\vec{n}|}\right) \quad \text{[Expression 4]}$$

Taking the coordinate of the related region of the subject tooth before the rotation correction as (x, y, z) and the coordinate of the related region of the subject tooth after the rotation correction as (x', y', z'), coordinate transformation is carried out in accordance with the following expression (5).

$(x' y' z') = (x y z)(M)$ where, [Expression 5]

$$(M) = \begin{pmatrix} v_x \cdot v_x \cdot (1-\cos\theta) + \cos\theta & v_x \cdot v_y \cdot (1-\cos\theta) - v_z \cdot \sin\theta & v_z \cdot v_x \cdot (1-\cos\theta) + v_y \cdot \sin\theta \\ v_x \cdot v_y \cdot (1-\cos\theta) + v_z \cdot \sin\theta & v_y \cdot v_y \cdot (1-\cos\theta) + \cos\theta & v_y \cdot v_z \cdot (1-\cos\theta) - v_x \cdot \sin\theta \\ v_z \cdot v_x \cdot (1-\cos\theta) - v_y \cdot \sin\theta & v_y \cdot v_z \cdot (1-\cos\theta) + v_x \cdot \sin\theta & v_z \cdot v_z \cdot (1-\cos\theta) + \cos\theta \end{pmatrix}$$

Here, although the related region after the rotation correction can be obtained by the expression (5) in theory, direct application of the process would be inconvenient in reality. In other words, the coordinate of the related region obtained after the rotation correction are integers, but calculation of the right side of the expression (5) will give real numbers. Therefore the obtained real numbers needs to be converted into integers. However, round-off errors will occur in the course of the conversion, leading to partial loss of information on the coordinate of the related region after the rotation correction. In order to avoid the problem, in the embodiment, each coordinate of the related region after the rotation correction is reversed and projected onto the coordinate before the rotation correction, and the pixel value of the projected coordinate is approximately calculated by linear interpolation. Such an inversion method is often used, and carried out, for example, in Patent Literature 9. Also, linear interpolation is a known method, and description thereof will be omitted.

Figures 13A, 13B, 13C:
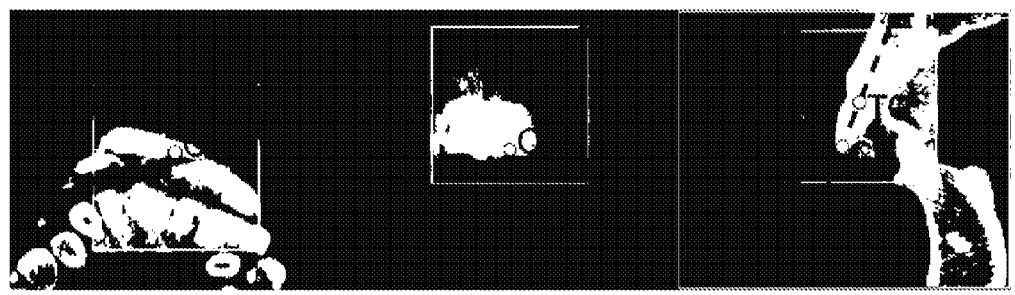
FIGS. 13a to 13c are views explaining input of a feature point for defining the principal axis of the subject tooth.
Figures 14A, 14B, 14C:
FIGS. 14a to 14c are views explaining how the principal axis of the subject tooth is corrected based on the feature point.

An example of a practical application of the rotation correction to a tooth #9 (left maxillary central incisor) on an actual X-ray CT image is shown. FIGS. 13a to 13c show images before the rotation correction, in which FIGS. 13a, 13b, and 13c respectively show A, C, and S cross-sections. FIGS. 13a to 13c are views in which the user has specified the Crown Centroid (CC), the Tooth Centroid (TC), and the size of the related region in advance while changing the position of the display cross-section. FIGS. 13a to 13c show three cross-sections such that the coordinate of the Crown Centroid (CC) is positioned at the center of the screen. Each cubic frame shown on the cross-sections indicates the related region. Also, in the example of FIGS. 13a to 13c, the Tooth Centroid (TC) is also at the same S cross-section, and a dashed line passing through the Crown Centroid (CC) and the Tooth Centroid (TC) is shown. The dashed line is the principal axis of the subject tooth. After this, the CPU 6 corrects the volume data in step S5, and the result is shown in each of FIGS. 14a to 14c. FIGS. 14a, 14b, and 14c respectively show A, C, and S cross-sections, and each of the figures shows the cross-section including the Crown Centroid (CC). In the C and S cross-sections of FIGS. 14b and 14c, the Tooth Centroids (TC) is also included on the same cross-section, and it can be seen that the entire related region has been corrected so as to align the principal axis of the subject tooth with the vertical direction of the screens.

Figures 15A, 15B, 15C, 15D, 15E:
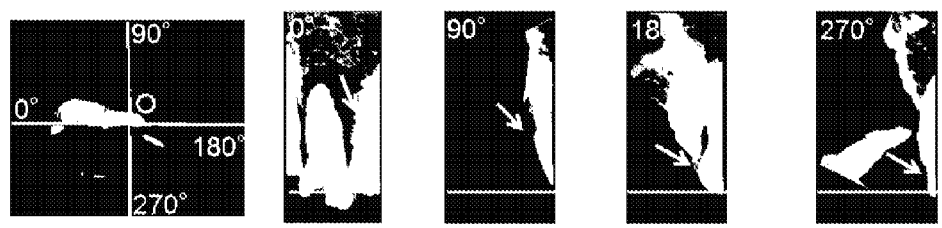
FIGS. 15a to 15e are views explaining generation of a rotated image.

In step S6, the image corrected in step S5 is rotated around the principal axis of the subject tooth while extracting a cross-section continuously, thereby generating a tomogram image. In this process, taking the vector v of the rotational direction as the vector n of the body axis, the expression (5) is applied while changing the rotation angle θ from 0 to 359° in 1-degree increments. After application of the expression (5), a cross-section is pulled out from the middle of the image and overlaid one on top of another into a tomogram image. FIGS. 15a to 15e are views explaining it. FIG. 15a shows an A cross-section including the Crown Centroid (CC) and has its center at the origin O. The half line extending leftward from the origin O is the initial line, and at this point, the rotation angle is 0°. Now, the half line will be rotated clockwise. One can imagine that while the half line is rotated around the origin O shown in the A cross-section of FIG. 15a from the rotation angle of 0° to 359°, the pixels on the half line are extracted. The half lines at the rotation angles of 0°, 90°, 180°, and 270° in FIG. 15a respectively correspond to those on FIGS. 15b to 15e. It is to be noted that an application of the process to a single A cross-section only provides the pixels at the positions shown by the half line in each of FIGS. 15a to 15e, but in reality, the related region of the subject tooth is a tomogram image in which several tens to hundreds of A cross-sections are overlaid, so an application of the process to the entire tomogram image provides cross-sections as shown in FIGS. 15b to 15e. Arrows shown in FIGS. 15b to 15e indicate the subject tooth, and the right end of each cross-section is the principal axis of the subject tooth. In the embodiment, the tomogram image is referred to as a rotated image. Similarly to the description of the above transformation, in the embodiment, each coordinate of the rotated image is calculated by the method of inverting each coordinate and projecting the principal axis of the subject tooth onto the coordinate after the rotation correction.

Figure 16:
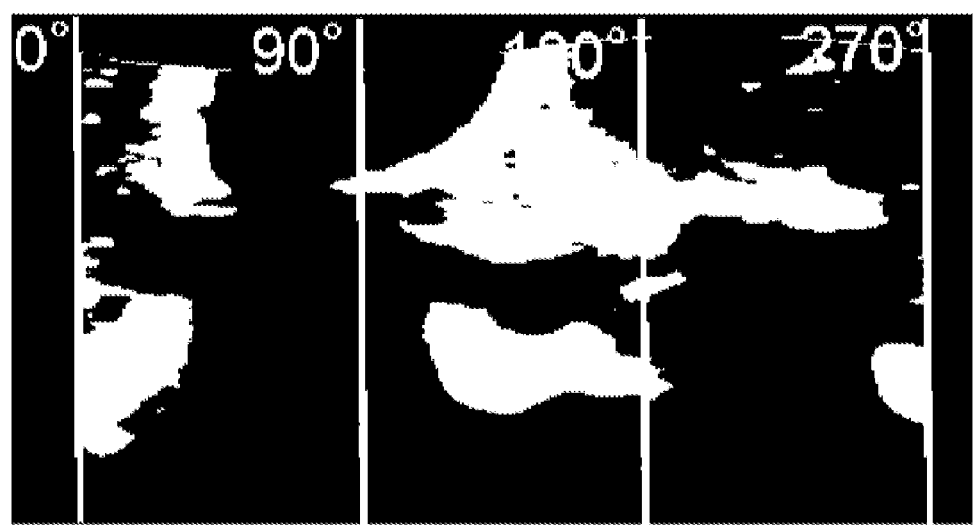
FIG. 16 is a view explaining generation of a developed image.

One can also imagine that in the rotated image, cross-sections obtained by slicing the image from different directions are overlaid one on top of another. FIG. 16 shows an example of a cross-section obtained by slicing the image such that pixels at an equal distance from the principal axis of the subject tooth form a cross-section. The half line at the rotation angle of 0°, 90°, 180°, and 270° in FIG. 16 correspond to those in FIGS. 15a to 15e. FIG. 16 can be considered as an image obtained by developing the subject tooth 360° around the principal axis. FIG. 16 shows a single cross-section, but a plurality of similar cross-sections can be generated by varying the distance from the principal axis of the subject tooth. In the embodiment, the image obtained by overlaying such cross-sections such that the cross-sections have the same distance from the principal axis of the subject tooth is referred to as a developed image.

Figure 17:
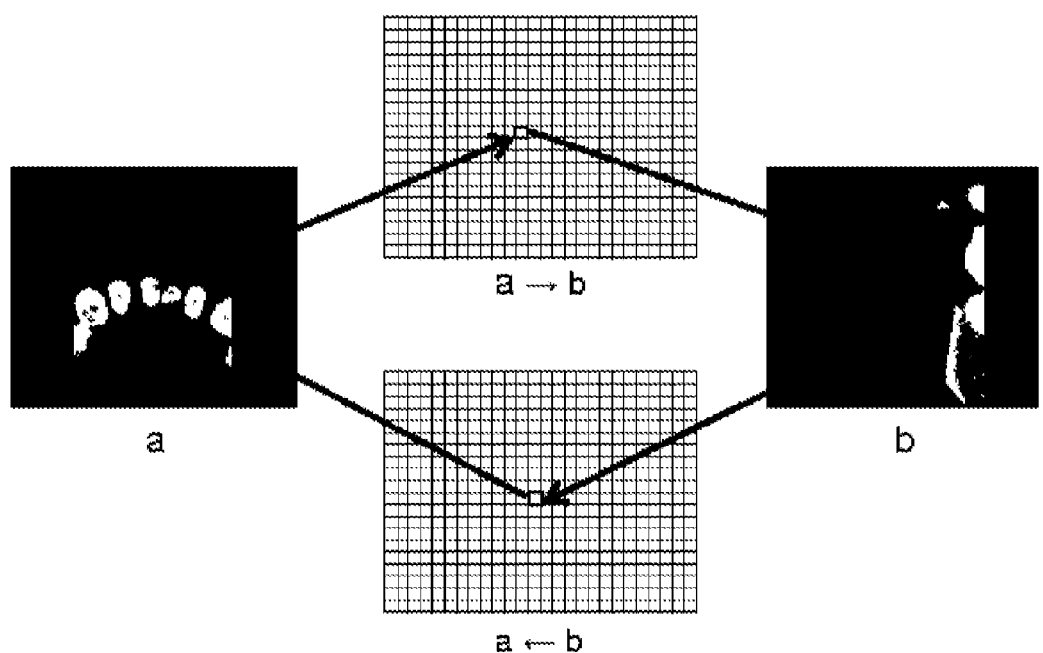
FIG. 17 is a view explaining transformation between a coordinate after rotation correction of the principal axis of the subject tooth and a coordinate of the rotated image (or the developed image).

FIG. 17 shows the relation between the tomogram image after the rotation correction of the principal axis of the subject tooth and the rotated image. What is displayed as "a" in FIG. 17 (hereinafter, referred to as "a" portion in FIG. 17) shows a cross-section of the tomogram image after the rotation correction of the principal axis of the subject tooth, and what is displayed as "b" in FIG. 17 (hereinafter, referred to as "b" portion in FIG. 17) shows a cross-section of the rotated image. A correspondence between the coordinate after the rotation correction of the principal axis of the subject tooth and the coordinate of the rotated image (the same applies to the developed image) is constant, and the correspondence is to be entered into a lookup table when generating the rotated image in step S6 (the same applies to the developed image). Here the lookup table means a data array which is obtained by mapping input values to output values and approximating the mathematical relationship. Also, the procedure of, when an input value is provided to the lookup table, obtaining the corresponding output value from the table is called a lookup operation. The CPU 6 performs the lookup operation to obtain a correspondence, when required by the alveolar bone convex-concave shape visualization device 3.

In the embodiment, a lookup table which is convertible bidirectionally as shown in FIG. 17 is created because the coordinate after the rotation correction of the principal axis of the subject tooth and the coordinate of the rotated image (the same applies to the developed image) need to be converted to each other in the following processes. Here, in the lookup table, an output value needs to be one value for an input. As described above, in the embodiment, in reality, the rotated image (the same applies to the developed image) is reversed to obtain the coordinate after the rotation correction of the principal axis of the corresponding subject tooth. Accordingly, the lookup table from "a" portion in FIG. 17 to "b" portion in FIG. 17 can be easily made. However, the coordinate after the rotation correction of the principal axis of the subject tooth might correspond to more than one coordinate of the rotated image (the same applies to the developed image), making it difficult to output strictly only one value. In the embodiment, if a plurality of outputs are calculated, it is supposed that the positions of those coordinates are adjacent to each other, and it is only needed that any one of the coordinates be entered into the lookup table from "a" portion to "b" portion in FIG. 17.

Figure 18:
FIG. 18 is a view showing an example of displaying cross-sections of a tomogram image obtained after the rotation correction of the principal axis of the subject tooth, the rotated image, and the developed image, where the cross-sections are displayed side by side on a screen.

In step S7, cross-sections acquired by the above method, namely, an A cross-section, a C cross-section, an S cross-section, a cross-section of the rotated image, and a cross-section of the developed image are displayed side by side on the screen. FIG. 18 shows an example in which the cross-sections are displayed side by side on the screen. In FIG. 18, the A cross-section, the C cross-section, the S cross-section of the tomogram image after the rotation correction of the principal axis of the subject tooth, the cross-section of the rotated image, and the cross-section of the developed image respectively correspond to what are displayed as "a" to "e" in FIG. 18. Each of the above cross-sections is displayed as selected arbitrarily from the tomogram image constituted by a plurality of cross-sections.

Figure 19:
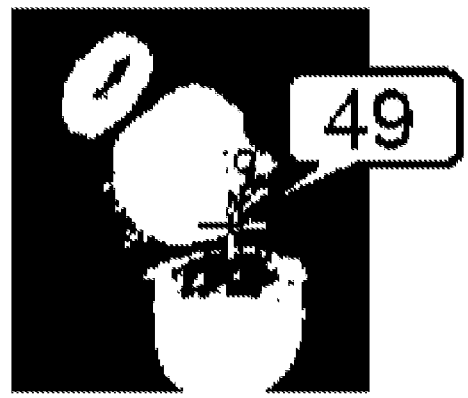
FIG. 19 is a view showing an example of a user controlling a mouse to specify a coordinate.
Figure 20:
FIG. 20 is a view showing an example of navigation of each screen when a user specifies a coordinate on an axial cross-section.
Figure 21:
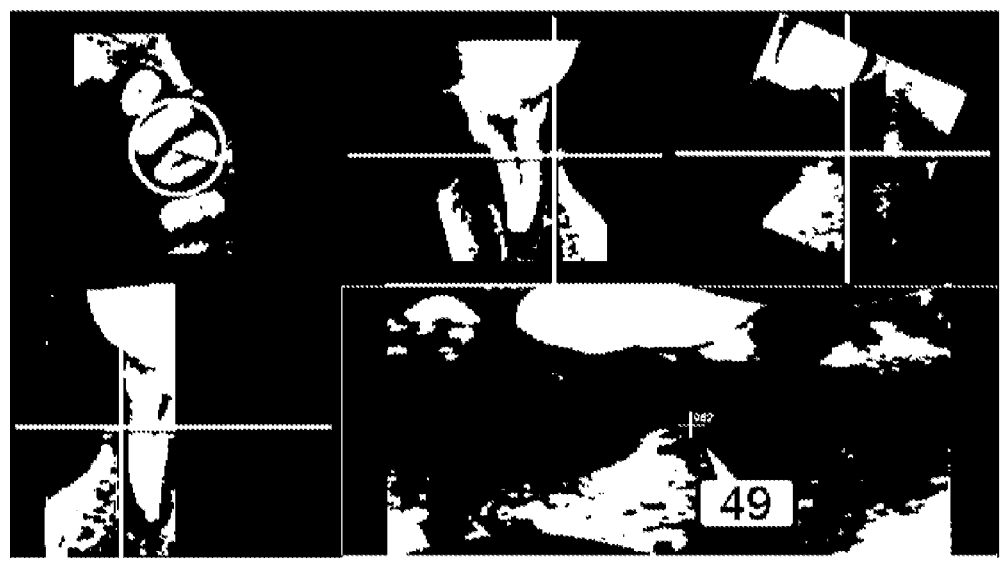
FIG. 21 is a view showing an example of navigation of each screen when a user specifies a coordinate on the developed image.

The screen of FIG. 18 includes the navigating function that will be described below. For example, as shown in FIG. 19, the user operates the mouse to move the mouse pointer over any position of the screen displaying the A cross-section, and presses the left mouse button. Then, the CPU 6 regards the coordinate as specified by the user and switches the four screens of the C cross-section, the S cross-section, the developed image, and the rotated image into cross-sections corresponding to the coordinate specified by the user. Further, while the mouse left button is held down, a cross line is displayed on each of the four screens. As for the A cross-section, a half line and a circle are displayed instead of the cross line. The half line and the circle are in contact with each other at the specified position, and respectively correspond to the positions of the displayed cross-sections of the rotated image and the developed image. FIG. 20 shows an example in which the five screens are displayed when the user has moved the mouse pointer over the A cross-section and is holding down the mouse left button. The intersections of the cross lines and the contact part of the half line and the circle on the five screens in FIG. 20 all represent the same coordinate specified by the user. As an example where a coordinate has been specified in any of the four screens except the A cross-section, FIG. 21 shows an example in which a coordinate has been specified on the screen of the developed image. In this case, the operation is almost similar to that in the case where a coordinate has been specified on the A cross-section, but the cross-line does not appear on the cross-section on which the user has specified the coordinate. This is because there is a mouse pointer on the cross-section and so the user knows the specified position without the cross line. When the user releases the left mouse button, these cross lines, the circle, and the half line disappear.

Figure 22A:
FIGS. 22a to 22c are views explaining how the cross-section of the developed image switches when the user drags while holding down the left mouse button on the axial cross-section.
Figure 22B:
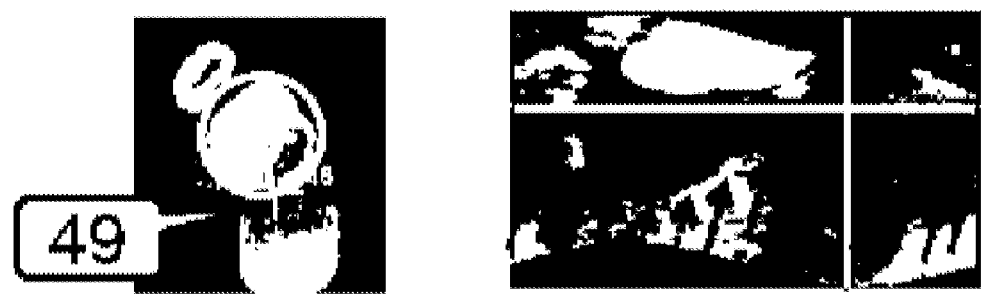
Figure 22C:
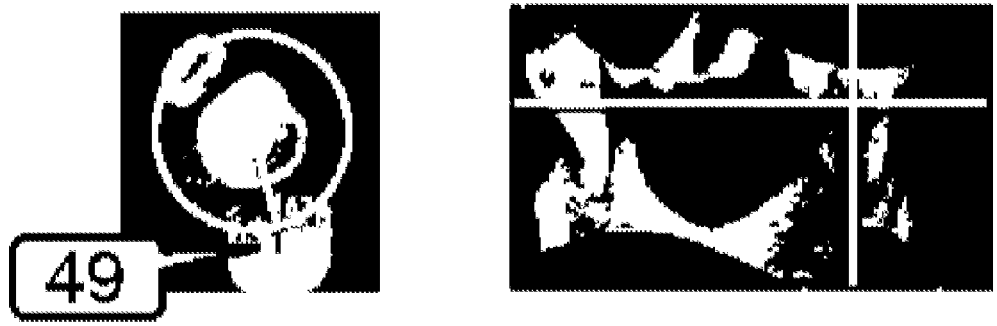

When the user drags while holding down the left mouse button (to move the mouse pointer while holding down the left mouse button) on the screen of FIG. 18, the CPU 6 regards, every time the mouse pointer position is updated, the position after the movement as specified by the user and switches each screen to a cross-section corresponding to that position. FIGS. 22a to 22c shows how the cross-section of the developed image switches when the user drags the mouse pointer on the A cross-section. In FIGS. 22a to 22c, images on the left are A cross-sections and those on the right are cross-sections of the developed image. In the example, the mouse is dragged from a portion close to the center of the tooth axis of the subject tooth toward the neighboring teeth, FIGS. 22a, 22b, and 22c are A cross-sections and cross-sections of the developed image which are obtained at the moment when the mouse pointer is moved to a portion close to the tooth axis of the subject tooth, a portion contacting the neighboring teeth, and the neighboring teeth, respectively. The intersections of the cross lines shown on the developed images indicate the specified coordinate. Looking at the developed cross-sections, FIG. 22a shows a cross-section obtained by developing the subject tooth. FIG. 22b shows a screen obtained by developing of an area close to the portion contacting the neighboring teeth, in which convex and concave of the alveolar bone crest along the entire circumference of the subject tooth can be observed as shown by a dash lined arrow. FIG. 22c shows a developed cross-section including the neighboring teeth, in which the two neighboring teeth on the mesial and distal sides can be seen. FIGS. 22a to 22c only show the A cross-sections and the cross-sections of the developed image at certain three moments, but in reality, five screens including all of the A cross-section, the C cross-section, the S cross-section, the cross-section of the rotated image, and the cross-section of the developed image are updated in real time as the mouse pointer moves. Accordingly, with the present embodiment, the user can grasp the convex and concave shapes of the alveolar bone crest three-dimensionally by observing these five screens while moving the mouse pointer in any direction.

Figure 23:
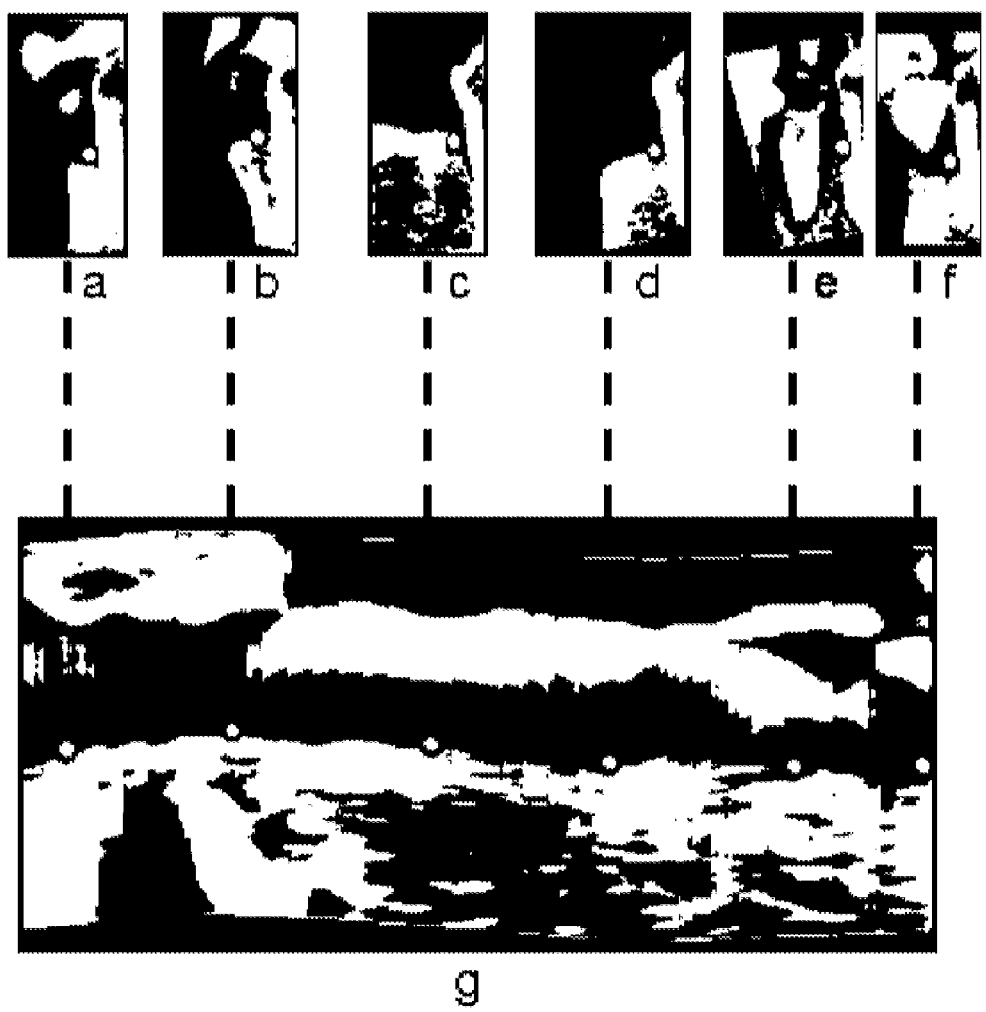
FIG. 23 is a view showing an example of displaying a cross-section of a developed image customized according to an input of an alveolar bone crest by the user.

Because the real contour of a tooth observed in a cross-section orthogonal to the principal axis is not a perfect circle, the user needs to observe a plurality of cross-sections for understanding the convex and concave shapes of the alveolar bone crest from the developed image. So, the alveolar bone convex-concave shape visualization device 3 may include the following functions on the screens of FIG. 18. First, a plurality of cross-sections are selected from the rotated image. The plurality of cross-sections are to be selected such that the selected images cross-sections not biased with respect to the entire circumference of the subject tooth. The user specifies the position of the alveolar bone crest at each selected cross-section. An example is shown in FIG. 23. What are displayed as "a" to "g in FIG. 23 (hereinafter, referred to as "a" to "g" portions in FIG. 23, respectively) are the cross-sections selected by the user, in each of which the coordinate specified as the position of the alveolar bone crest is shown by a circular shape. In this example, six images are selected out of 360 cross-sections constituting the rotated image. The position of the alveolar bone crest in the remaining 354 cross-sections will be determined by linear interpolation based on the position of the alveolar bone crest specified by the user in the adjacent cross-sections. In this way, the position of the alveolar bone crest is determined in all cross-sections constituting the rotated image. Next, each cross-section of the rotated image is moved horizontally so as to show the positions of the alveolar bone crest of each cross-section on the same cross-section of the developed image, and thus this is displayed as a cross-section of the developed image. The result of the process is shown "g" portion in FIG. 23. In FIG. 23 "g" portion is a cross-section of the developed image, and circular shapes shown in the cross-section correspond to those of "a" to "f" portions in FIG. 23 right above them. Looking at "g" portion in FIG. 23, the alveolar bone crests specified by the user in "a" to "f" portions in FIG. 23 can be seen in a developed manner, and thus the user can easily understand the convex-concave shape.

REFERENCE SIGNS LIST

1 . . . Medical image processing apparatus
2 . . . DICOM file
3 . . . Alveolar bone convex-concave shape visualization device
4 . . . Display monitor
5 . . . Image inputting section
6 . . . CPU
6a . . . Volume data manipulating means
6b . . . Navigation means
7 . . . Processing program storing section
8 . . . Display processing section
9 . . . Storing device interface
10 . . . Hard disk
11 . . . Input operation section
12 . . . Data path
30 . . . Tooth
31 . . . Root
32 . . . Gingiva (gums)
32a . . . Periodontal ligament
33 . . . Cervical portion
34 . . . Root apex
35 . . . Alveolar bone
35a . . . Alveolar bone crest portion
36 . . . Region surrounded by alveolar bone
37 . . . Crown
40 . . . Tooth
45 . . . Pocket
46 . . . Gingiva (gums) top
47 . . . Pocket bottom
48 . . . Blood and pus
49 . . . Mouse pointer
50 . . . Plaque accumulation
51 . . . Gingiva inflammation
52 . . . Destruction of alveolar bone

The invention claimed is:

1. A periodontal disease testing apparatus comprising: an X-ray CT scanner photographing a portion including a tooth, a gingiva, and alveolar bone within an oral cavity to generate volume data of the portion; region setting means setting a related region of a subject tooth based on the volume data; defining means defining a principal axis of the subject tooth; correcting means correcting the related region so as to align the principal axis of the subject tooth with a normal direction of a cross-section of an X-ray CT image; multi-planar reconstruction image generating means generating a multi-planar reconstruction image of the corrected related region; means for generating a tomogram image transforming a coordinate of the related region to generate a developed image and a rotated image; and navigating means indicating correspondences of a spatial coordinate among the multi-planar reconstruction image, the developed image, and the rotated image; wherein when a part or all of five screens of an A cross-section, a C cross-section, an S cross-section, a cross-section of the developed image, and a cross-section of the rotated image are displayed, a user specifies a position on any one of the screens, the navigating means switches remaining screens to cross-sections which show the position specified by the user and show the positions with intersections of cross lines or a contacting part of a circle and a half lin.

2. The periodontal disease testing apparatus according to claim 1, wherein
when a user inputs two feature points with respect to the subject tooth, the region setting means sets a cubic region with the input point at a center.

3. The periodontal disease testing apparatus according to claim 1, wherein
the defining means defines the principal axis with a segment connecting two feature points input by the user as a unit vector.

4. The periodontal disease testing apparatus according to claim 1, wherein
the correcting means performs a rotation correction process on the related region so as to align the principal axis with a normal vector of cross-sections constituting an A tomogram image of the X-ray CT image.

5. The periodontal disease testing apparatus according to claim 1, wherein
the multi-planar reconstruction image generating means generates another tomogram image with which an A cross-section, a C cross-section, and an S cross-section corresponding to any position of the related region after an application of the rotation correction process can be displayed.

6. The periodontal disease testing apparatus according to claim 1, wherein
the means for generating a tomogram image creates cross-sections while rotating the related region after the application of the rotation correction process about the principal axis and overlays the cross-sections such that the cross-sections have the same distance from the principal axis, thereby generating the tomogram image.

* * * * *